United States Patent [19]

Virag

[11] 4,105,029
[45] * Aug. 8, 1978

[54] INTRAVENOUS SOLUTION SET HAVING AN AIR ACCESS SITE AND CONSTRICTED INNER DIAMETER PORTION

[75] Inventor: Robert A. Virag, Lake Zurich, Ill.

[73] Assignee: Baxter Travenol Laboratories, Inc., Deerfield, Ill.

[*] Notice: The portion of the term of this patent subsequent to Jul. 12, 1994 has been disclaimed.

[21] Appl. No.: 791,674

[22] Filed: Apr. 28, 1977

Related U.S. Application Data

[63] Continuation-in-part of Ser. No. 602,614, Aug. 7, 1975, Pat. No. 4,034,754.

[51] Int. Cl.² ............................................. A61M 5/00
[52] U.S. Cl. ................................. 128/214 R; 128/221
[58] Field of Search ............... 128/214, 214 C, 214.2, 128/213, 214 E, 214 F, 221, DIG. 23

[56] References Cited

U.S. PATENT DOCUMENTS

| | | | |
|---|---|---|---|
| 3,675,891 | 7/1972 | Reynolds | 128/214 R X |
| 3,677,242 | 7/1972 | Shaye | 128/214 C |
| 3,803,914 | 4/1974 | Noiles | 128/214 C |
| 3,878,869 | 4/1975 | Yamanouchi et al. | 128/214 R X |
| 3,886,937 | 6/1975 | Bobo | 128/214 R |

Primary Examiner—Stephen C. Pellegrino
Attorney, Agent, or Firm—Paul C. Flattery; John P. Kirby, Jr.; Gary W. McFarron

[57] ABSTRACT

A parenteral liquid infusion set comprising flow tubing as an intermediate site for the potential access of air suitable for connection with another set or the like, and a drip chamber upstream thereof having a constricted drop-forming member. To avoid the possibility of suction of air through the air access site, a tubing section of constricted bore is provided downstream from the potential air access site and so proportioned as to cause the pressure drop of the portion of the set upstream from the potential air access site to be always less than the pressure drop of the portion of the set downstream from the potential air access site under conditions of normal use and specifically under a precise set of test conditions.

4 Claims, 3 Drawing Figures

U.S. Patent    Aug. 8, 1978    4,105,029
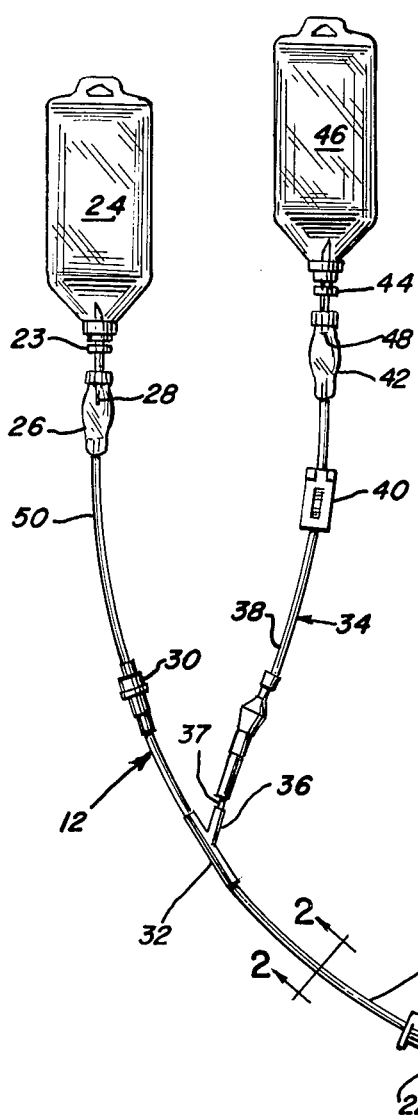
FIG. 1
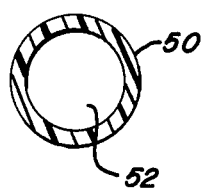
FIG. 2
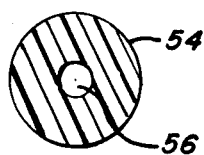
FIG. 3
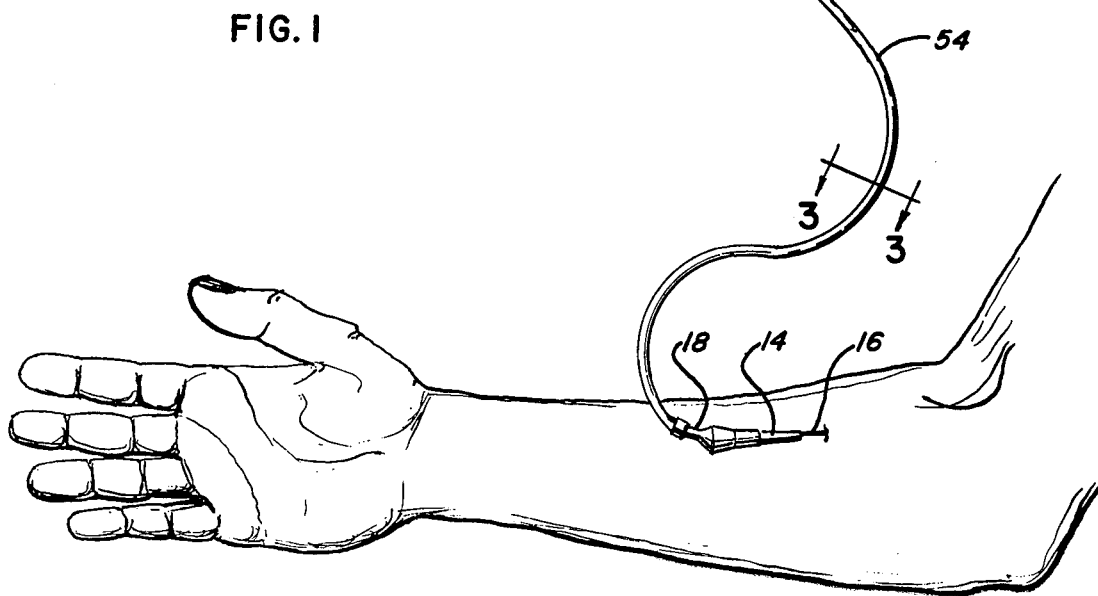

INTRAVENOUS SOLUTION SET HAVING AN AIR ACCESS SITE AND CONSTRICTED INNER DIAMETER PORTION

CROSS-REFERENCE TO RELATED APPLICATION

This application is a continuation-in-part of application Ser. No. 602,614, filed Aug. 7, 1975 now U.S. Pat. No. 4,034,754.

BACKGROUND OF THE INVENTION

In the administration of intravenous fluids such as parenteral solutions, physicians frequently desire a connection of two different containers of parenteral solution to the same set, which communicates with a single intravenous needle in communication with the venous system of a patient. For example, the CONTINU-FLO$^{T.M.}$ intravenous solution set, sold by Travenol Laboratories, Inc. of Deerfield, Illinois, utilizes fluid flow tubing having a connector on one end for connection with a parenteral solution bag or bottle, and a needle adaptor on its other end for intravenous connection with a patient. A Y-site is positioned on the set, capable of connection with an ADD-A-LINE$^{T.M.}$ intravenous solution set, which is also sold by Travenol Laboratories. This latter set is capable of connection at its other end with a second parenteral solution source.

Accordingly, a set-up of the two above-mentioned parenteral solution sets can be used to administer two different solutions. For example, the CONTINU-FLO set may be connected as a first set to a container of normal saline or dextrose solution. The ADD-A-LINE set may be connected, as a second set in connection with the first set, to a container of antibiotic solution. Hence, a slow, continuous drip of normal saline or dextrose may be administered to the patient, for maintenance of an effective parenteral liquid connection with the patient's venous system. This permits the immediate, intermittent administration of the antibiotic as needed over a period of time.

While a continuous drip of normal saline or dextrose solution is required for preventing blood clotting in the needle, it is generally desired for the overall amount of such solution administered on a continuous basis to be very small. In fact, frequently, the desired flow rate can be so low that the conventional drip chamber of an administration set forms drops (about 10 drops per c.c. of fluid administered) which are large enough to fall so infrequently from the drop former of the drip chamber that it becomes difficult and time-consuming to accurately measure the drip rate. Accordingly, the overall fluid administration rate of the set is not easily monitored.

In response to this, parenteral administration sets are sold in which a small drop forming tube is utilized in the drip chamber. This tube may have an inner diameter of typically about 0.02 to 0.03 inch. Such a constricted drop forming chamber in a drip chamber is capable of producing smaller drops, for example, about 60 drops per c.c. of liquid administered. Accordingly, at the same low flow rate, drops of liquid will fall through this drip chamber at a rate six times faster than they would through a large drop forming a drip chamber of ten drops per c.c.

While the above small-drop arrangement is a satisfactory solution for the determination of flow through an administration set at low flow rates, a problem is created in the situation where a pair of solution sources are connected together for intermittent, alternate fluid administration to a patient through a single needle. The problem is that, when a small drop forming member is used in a drip chamber, and a higher overall fluid flow is desired, a suction pressure head can develop in the tubing downstream from the drip chamber. This is so because the small drop forming member may provide an inadequate fluid flow to resupply the set, as solution is administered at a high rate to a patient, impelled by the gravity pressure of the fluid column in the administration set (or alternatively by a pump).

As a result of this, in gravity-operated sets, if the connection site of the second set with the first set is positioned remotely from the patient and near the drip chamber mentioned above, and if the parenteral solution source connected to the second set becomes empty, air may be sucked into the parenteral solution set through the second set. The same event can also take place in pumped sets.

Thereafter, the administration of a second aliquot of solution from the first source of parenteral solution may actually cause air to be forced into the patient, which is extremely undesirable and dangerous. Alternatively, if the presence of air is noticed, the sets may have to be disconnected and reprimed to eliminate air.

The above problem exists whenever an air access site exists in the set, particularly in its upper portion in position of use, where a substantial suction pressure head can form to cause air to be drawn into the set.

While this problem can, in gravity operated sets, be reduced in scope when the access site is positioned lower and nearer to the patient, this can be undesirable, since it brings the site within reach of the patient, and thus is more subject to being tampered with and the like. Furthermore, a downstream connection of primary and secondary sets produces more of a tangle of tubing at the patient's bedside.

The invention of this application overcomes the above difficulties, in that it provides, for the first time, a means whereby an administration set may be safely used with a patient, even though (1) a constricted drop-forming member is used, and (2) an air-access site to the set is vertically elevated, near the drip chamber and the hanging sources of parenteral solution, and away from the patient.

Accordingly, by this invention, the advantages of a constricted drop-forming member of the drip chamber can be achieved, without running the risk of infusing air into the patient. This has hitherto been inherent in the use of such a small-drop drip chamber in conjunction with a connected pair of sets and separate sources of parenteral solution.

DESCRIPTION OF THE INVENTION

The invention of this application relates to a parenteral liquid infusion set which comprises flow tubing, means for connection at one end of the flow tubing with blood vessel penetrating means, and means for connection with a parenteral liquid source at the other end of the tubing. A drip chamber is also provided, having a tubular drop-forming member of reduced inner diameter relative to the normal inner diameter of the flow tubing. As intermediately-positioned air-access site between the exterior and the interior of the set is present, being positioned downstream from the drip chamber in the direction of the set end which is designed to carry the blood vessel penetrating means (such as a needle).

This access site may be a sealed connection site for a second set, a porous in-line filter housing, or the like.

In accordance with this invention, a portion of fluid flow tubing positioned downstream from the air access site, which may be positioned in the upper half of the set, defines a bore of reduced diameter, when compared with the bore size of the remainder of the flow tubing, which reduced diameter bore is of a length and diameter to cause the overall frictional pressure drop of water in the portion of the set which is upstream from the intermediately-positioned site to be less than the frictional pressure drop of water through the portion of the set which is downstream from the intermediately-positioned site, when the set is extended in a fully vertical position, and the means for connection with a parenteral liquid source is connected with a vented solution container in which the liquid level of solution in the container is no higher than the upper end of the connection means with the parenteral liquid source, and while no outside clamping restriction to flow is applied to the set.

Accordingly, air will not be sucked into the flow tubing through any air-access site such as an administration set connected with an intermediately-positioned connection site, even if such administration set is emptied of solution.

In the drawings,

FIG. 1 is an elevational view of one embodiment of a parenteral fluid infusion set of this invention, shown connected at its respective ends with a first source of parenteral solution and the venous system of the patient, with a second parenteral liquid infusion set and a second source of parenteral liquid being shown in fluid communication with the set of this invention through an intermediately-positioned connection site.

FIG. 2 is an enlarged sectional view of the set of this invention, taken along line 2—2 of FIG. 1.

FIG. 3 is an enlarged sectional view of the set of this invention, taken along line 3—3 of FIG. 1.

Referring to the drawings, set 10 is shown comprising flow tubing 12, which typically may comprise vinyl plastic tubing of a conventional flexible type. A needle adapter 14 is provided at one end of the set, shown in the present embodiment to carry an intravenous needle 16, which, in turn, is shown to be penetrating the venous system of a patient. A typical latex blood flashback site 18 is also provided.

An auxiliary, supplementary medication Y-site 20 may be positioned as shown in the set, as well as a roller clamp 22 or another, equivalent clamp for controlling the overall flow of solution to the patient.

At the other end of set 10, a conventional connection spike 23 penetrates a parenteral solution container 24 for access to the contents thereof. Drip chamber 26 is provided, including a tubular, drop-forming member 28, which is typically a metal sleeve having a reduced inner diameter of 0.023 inch in the embodiment shown, to form about 60 drops per c.c. of fluid passing through it.

A one-way valve 30, typically of the duckbill type, is provided as shown to prevent parenteral solution from backing up into container 24.

In the embodiment of FIG. 1, the intermediately-positioned site providing potential access of air to the interior of the set from the exterior is a branched connection site of conventional construction for connection with second parenteral solution administration set 34. Prior to connection with set 34, connection site 32 carries a sealing member in arm 36 which seals the set from the exterior, but permits access to the interior by set 34 through access needle or spike 37.

Second set 34 is, as mentioned above, a conventional administration set defined by flexible tubing 38, including roller clamp 40, or any other equivalent flow control means, and drip chamber 42. Piercing spike 44 is shown in connection with a second source of parenteral solution 46.

The drop-forming member 48 of drip chamber 42 may be of any desired inner diameter for forming drops of an appropriate size.

The parenteral solution source 46 is shown to be at an elevated height in position of use with respect to solution source 24, to provide an increased pressure head through set 34. It is for this reason that one-way valve 30 is present, to prevent solution from set 34 from passing upwardly toward first parenteral solution source 24 when clamp 40 is opened.

In accordance with this invention, a first, upper length of tubing 50 of set 10 has a relatively and conventionally large diameter of bore 52, as shown in FIG. 2, for example from 0.05 to 0.15 inch in diameter, and specifically 0.10 inch in diameter. Such conventional tubing may have a wall thickness of about 0.01 to 0.025 inch, the preferred wall thickness being about 0.019 inch.

Another length of tubing 54 of set 10 defines a bore 56 of restricted diameter, as shown in FIG. 3. This length of flexible tubing 54 is at least two and preferably at least five inches in length, and defines a bore typically of about 0.01 inch to 0.04 inch in diameter. As a specific example, tube section 54 may be twelve inches in length and may define a bore 56 having a diameter of 0.028 inch. Tubing 54 may be colored for identification.

As a result, the overall flow through set 10 is restricted by the length of tubing 54 to a degree necessary to prevent the creation of less than atmospheric pressure in the vicinity of connection site 32, caused by gravity suction produced by the column of liquid in the set below connection site 32, when, for example, clamp 22 is in wide open configuration. Without tubing 54, if such a subatmospheric pressure were allowed to be created, when container 46 runs dry, it would be possible for air to pass through set 34 into set 10 if clamp 22 remains in the open position. The air could then be driven into the patient by the weight of additional parenteral solution from solution source 24, overcoming the venous pressure of the patient, and forcing air bubbles into the patient.

When a properly proportioned section of constricted tubing 54 is provided, such a reduced pressure cannot be created, and accordingly air is not sucked into the set through site 32. The appropriate amount of flow restriction can be easily controlled by lengthening or shortening tubing 54. This correspondingly increases or reduces the flow restriction without the need to replace tubing 54 with tubing having a different bore size.

Also, tube section 54 reduces the possibility of accidentally "flooding" the patient with an excessive inflow of parenteral solution. Furthermore, sets utilizing this invention can be flow-controlled by changing the elevation of containers 24, 46.

As a further advantage, tubing 54, preferably having an increased wall thickness of about 0.04 to 0.08 inch, and typically about 0.057 inch, does not as easily kink when placed in U-shaped configuration on the patient's arm, when compared with conventional tubing.

If desired, site 32 can be replaced with a venting, in-line filter type device, for the removal of air from administration sets. Also, site 32 can be replaced with any other connection site providing the possibility of air-access, such as a T-shaped site, a latex injection bulb, filter housings with integral injection sites, or pre-attached supplemental medication sets like set 34.

The specific design of an administrative set, in accordance with this invention, may be developed by the mathematical model described below. Basically, by the following mathematical model, the necessary impedence to flow, in terms of length of constricted tubing or other means of restriction, for any desired result and margin of safety may be calculated for any specific reduced bore size and length of constricted tubing or for any other restrictive geometry.

Basically, this is accomplished by experimentally determining the impedence to flow of each component with "non-standard" geometry of the proposed set. Standard geometry components of the set can be analytically determined. Then, the sum of the component impedences upstream of the intermediately-positioned site 32 including the site 32, are analyzed using Bernoulli's equation to determine a velocity that will produce a pressure just equal to atmospheric at the intermediately-positioned site 32. Thereafter, the sum of the total component impedences are integrated together using Bernoulli's equation with the geometry of the constricted tubing 54 or other restriction as the only unknown. Solving this equation yields the geometry of the restrictor required to produce a velocity and flow rate such that a pressure just equal to atmospheric exists at the intermediately-positioned site; assuming laminar flow through a fully vertically extended, draining set with clamps wide open, so as not to provide any outside restriction to the vertical set.

Bernoulli's equation, as applied to each component in the solution set, is expressed as follows:

$$\frac{V_1^2}{2G} + \frac{P_1}{eG} + Y_1 = \frac{V_2^2}{2G} + \frac{P_2}{eG} + Y_2 + F\left(\frac{L}{D}\right)\frac{V_2^2}{2G} \quad (1)$$

Where subscripts 1 and 2 refer to two points on the same streamline, $V_1$ = Velocity initial (FT/SEC)
$P_1$ = Pressure initial (LBS/FT$^2$)
$P$ = Density of fluid (LBS/FT$^3$)
$G$ = 32.2 (FT/SEC$^2$)
$Y_1$ = Height (FT)
$V_2$ = Velocity final (FT/SEC)
$P_2$ = Pressure final (LBS/FT$^2$)
$Y_2$ = Height (FT)
$F$ = Friction factor (Dimensionless)
$L$ = Component length (FT)
$D$ = Component inside diameter (FT)
$\rho$ = Density of the fluid (Slugs/Ft$^3$)

Application of Bernoulli's equation to a practical situation can be accomplished by making initial assumptions:

(1) $V_1$ = Velocity at the surface of the fluid in the bottle or bag and is assumed equal to zero.

$$P_1 = P_2 \quad (2)$$

(3) Assume kinetic losses through area changes are negligible.

(4) $Y_2 - Y_1$ = Head pressure (H).

(5) Assume laminar steady-state flow.

(A) Laminar flow states that component friction (F) is equal to 64 divided by the Reynold's number.

(B) The Reynold's number ($N_{RE}$) is defined by the equation:

$$N_{RE} = (\rho VD/\mu) \text{ (DIMENSIONLESS)} \quad (2)$$

Where:
$\rho$ = Density of fluid (SLUGS/FT$^3$)
$V$ = Velocity through component (FT/SEC)
$D$ = component inside dia. (FT)
$\mu$ = Absolute viscosity of the fluid (LBF-SEC/FT$^2$)

(C) Therefore, the component friction may be defined by:

$$F = (64/N_{RE}) = (64\mu/\rho VD) \quad (3)$$

Combining these assumptions in Bernoulli's equation yields:

$$\frac{(V_f)^2}{2G} + \left[\frac{64(\mu/\rho)L_1}{2G(D_1)^2}V_1 + \frac{64(\mu/\rho)L_2}{2G(D_2)^2}V_2 + \ldots + \frac{64(\mu/\rho)L_f}{2G(D_f)^2}V_f\right] \quad (4)$$

Because of the number of different components in the set, it is much easier to determine the velocities through each component in terms of the final velocity, i.e., the velocity through the last component, which may be needle 16. This is accomplished by applying the continuity equation. Simply stated, the mass flowing past any one section of a duct or conduit is the same as that past any other section.

Mathematically:

$$\rho_1 V_1 A_1 = \rho_2 V_2 A_2$$

where,
$\rho_{1,2}$ = Density (LBS/FT$^3$)
$V_{1,2}$ = Velocity (FT/SEC)
$A_{1,2}$ = Area (FT$^2$)

Let $\rho_1 \cong \rho_2$ because the fluid density is assumed constant. Then:

$$V_1 A_1 = V_2 A_2$$

so, $$V_1 = (A_2/A_1)V_2$$

Therefore, where $V_f$ = final velocity (FT/SEC):

$$\frac{(V_f)^2}{2G} + V_f\left[\frac{64(\mu/\rho)L_1}{2G(D_1)^2}\left(\frac{A_f}{A_1}\right) + \ldots + \frac{64(\mu/\rho)L_f}{2G(D_f)^2}\left(\frac{A_f}{A_f}\right)\right] - H = 0 \quad (5)$$

We define $\beta$ (Beta) as equal to $$\frac{64(\mu/\rho)L}{2GD}\left[\frac{\text{(FT-H}_2\text{O FT)}}{\text{SEC}}\right]$$

and using a shorthand notation for summantion, the governing equation becomes:

$$\frac{(V_f)^2}{2G} + V_f \sum_{i=1}^{i=n} \beta_i \left(\frac{A_f}{a_i}\right) - H = 0$$

where $i$ represents each component (In the specifice set of FIG. 1, $n$ equals 12, since there are twelve components).

The column height in the secondary set must also be analytically determined. From fluid dynamics, the total pressure is equal to the sum of static pressure, velocity pressure, and the frictional pressure loss. Mathematically:

$$P_T = P_S + P_V + P_{FRICTION}$$

where, $P_T$ = Total Height (FT of $H_2O$)
$P_S$ = Static pressure (FT of $H_2O$) defined as the pressure seen if flow were stopped
$P_V$ = Velocity pressure (FT of $H_2O$)
$P_{friction}$ = Frictional pressure loss (FT of $H_2O$)

$$= F(L/D)(V^2/2G)$$

Because of low velocity we can state that $(V^2/2G)$ is negligible, so, $$P_T = P_S + P_{friction}$$

The design requirement then is to keep the static pressure at the V-site greater than or equal to zero. Mathematically, $$P_S = P_T - P_{friction} \geq 0$$

It is also desirable to include a factor of safety to insure conformance to design parameters. The total pressure available at the intermediate site 32 is a liquid level from site 32 to the bottom of the bottle or bag 24 in the worst case. In this state, safety requires a certain fluid level in the secondary set 34 (i.e. the secondary set acts as a manometer).

Each component of the set 12, or any set, has manufacturing tolerances that affect its impedence to flow. Standard engineering procedure should account for the "worst" case and design accordingly. This is accomplished by evaluating the maximum and minimum expected impedence to flow and applying Bernoulli's equation for both cases.

It must also be pointed out that any restrictor analogous to tubing 54 that satisfies Bernoulli's equation will function according to the design parameters.

Specifically applying the above to the set shown in the drawings, each separate component of the set is separated, and the flow rate of water or normal saline is measured through the component at a known pressure head height, specifically nine inches. For those components which are of non-standard geometry, i.e. non-tubular in shape, the friction factor $\beta$ can be determined from the flow rate and other parameters by Bernoulli's equation through the testing of, for example, ten of each type of component at a nine inch liquid head. From the flow rates achieved, one then statistically determines the $3\Sigma$ variation. $\beta$ max is then identified as the larger $3\Sigma$ value i.e. the statistical value with respect to which 99 percent of components tested will have a lesser $\beta$, and represents the expected maximum pressure drop for the component being measured. The minimum area A of each component is also measured.

For the tubular components (of standard geometry) $\beta$ max can be calculated without experimental measuring, assuming laminar flow.

In the specific set disclosed in the drawings, the following data was obtained:

| Component | $\beta$ max (FT – $H_2O$). sec/ft. | $A_{min.}$ (FT$^2$) |
|---|---|---|
| Spike 23 | 0.012162 | 8.648 × 10$^{-5}$ |
| Drop-Forming Member 28 | 0.3058 | 2.761 × 10$^{-6}$ |
| Drip Chamber 26 | 0* | |
| Tubing 50 (Above Valve 30) | 0.7812 | 6.362 × 10$^{-5}$ |
| Duckbill Valve 30 | 0.744 | 1.772 × 10$^{-5}$ |
| Tubing 50 (below valve 30 and above site 32) | 0.003272 | 6.362 × 10$^{-5}$ |
| Access Site 32 | 0.0104 | 4.128 × 10$^{-5}$ |

*The drip chamber, which provides essentially no flow resistance, decreased the liquid head in the experiment by 0.1667 feet.

Applying this data to the sum of $\beta_i(A_f/A_i)$ for the above seven components of the set, down to the upper potential air access site 32, we obtained a value of $$6.374 \frac{(FT - H_2O) SEC}{FT^2},$$

which in turn equals $$76.488 \frac{(inches - H_2O) SEC}{FT}$$

Accordingly, $$P_{FRICTION} - V_f \sum_{i=1}^{i=7} \beta \left(\frac{A_f}{A_i}\right)$$

which is the upstream frictional head loss. When $P_{friction}$ equals fifteen inches of water, we determined $V_f$ in this circumstance to be 0.196 feet per second, which is the liquid velocity without restriction at site 32 when the set is about to drain container 24, and is fully vertical with clamp 22 fully open and with no other flow restriction. From this, the maximum theoretical flow rate which can pass through the set without causing aspiration of air at Y-site 32 when the empty set 34 is connected turns out to be 825 cc. per hour.

Now it is possible to build in any desired safety factor one wishes, to account for unfavorable factors which might cause aspiration. For example, it can be calculated that a flow rate of 715 cc. per hour through spike 32 should result in a liquid head up from site 32 in set 34 of no less than two inches in the worst cases.

Proceeding forward with this calculated flow rate, utilizing equation 6, we obtain: $0.0155V_f^2 + \beta V_f - H = 0$ Therefore, $\beta$ (total for the set) equals $$\frac{H - 0.0155V_f^2}{V_f}$$

We continue to measure $\beta$ min. and A max for the remaining components of set 10 in the manner previously described. The results were:

| Component | $\beta$max (FT − H$_2$O) sec/ft. | A min.(ft$^2$) |
|---|---|---|
| Tubing 50 (downstream) of site 32) | 0.51571 | 6.213 × 10$^{-5}$ |
| Injection site 20 | 0.378 | 1.327 × 10$^{-5}$ |
| Injection site 18 | 0.136 | 7.466 × 10$^{-5}$ |
| Needle 16 (18 gauge) | 0.17614 | 6.492 × 10$^{-6}$ |

With this information, it becomes possible to solve for (B min/A max) for tubing portion 54, using the definition of $\beta$ below equation 5, where the length (L) of tubing 54 is set at 23.5 inches, for example. In this circumstance B min/A max = 9.083 × 10$^{+5}$. From this, the diameter of bore 56, which is the largest diameter that will theoretically allow the set to drain container 24, while hanging fully vertically and maintaining a two inch head of liquid in set 34, is 0.029 inch.

As can be seen, the same process can be utilized to calculate a theoretical diameter for bores 56 of tubing sections 54 of different lengths, and for different sets having different components.

The above has been offered for illustrative purposes only, and is not for the purpose of restricting the scope of the invention of this application, which is as defined in the claims below.

That which is claimed is:

1. In a parenteral liquid infusion set which comprises flexible flow tubing, means for connection at one end of said flow tubing with blood vessel penetrating means, means for connection with a parenteral liquid source at the other end of said tubing, drip chamber means having a tubular, drop-forming member at an upper end thereof of reduced inner diameter relative to the inner diameter of said flow tubing, and an intermediately-positioned site providing potential access of air to the interior of said set from the exterior, said site being positioned downstream from said drip chamber, the improvement comprising, in combination: a portion of said flexible fluid flow tubing positioned downstream from said access site defining a bore of reduced diameter, when compared with the bore size of the remainder of said flow tubing, said reduced diameter bore being of a length and diameter to cause the overall frictional pressure drop of water in the portion of said set which is upstream from and including said intermediately-positioned site to be less than the frictional pressure drop of water through the portion of said set which is downstream from said intermediately-positioned site when said set is extended in a fully vertical position, and said means for connection with a parenteral liquid source is connected with a vented solution container in which the liquid level of solution in said container is no higher than the upper end of said means for connection with the parenteral liquid source, and while no outside clamping restriction to flow is applied to said set.

2. The parenteral liquid infusion set of claim 1 in which said intermediately-positioned site is positioned in the upper half of the set.

3. The parenteral liquid infusion set of claim 2 in which the wall thickness of said portion of the fluid flow tubing defining a bore of reduced diameter is greater than the wall thickness of the remaining tubing in the set.

4. The parenteral liquid infusion set of claim 3, connected to a second parenteral liquid infusion set through said intermediately-positioned site.

* * * * *